United States Patent

Dozol et al.

[11] Patent Number: 5,866,087
[45] Date of Patent: Feb. 2, 1999

[54] CALIXARENE DERIVATIVES, THEIR PREPARATION PROCESS AND THEIR USE FOR EXTRACTING ACTINIDES AND LANTHANIDES

[75] Inventors: Jean-François Dozol, Pierreuert; Hélène Rouquette, Manosque, both of France; Volker Böhmer, Mainz, Germany; Cordula Grüttner, Güstrow, Germany; Ralf A. Jakobi, Pirmasens, Germany; Dagmar Kraft, Detmold, Germany; Walter Vogt, Wiesbaden, Germany

[73] Assignee: Commissariat a l'Energie Atomique, Paris, France

[21] Appl. No.: 875,307

[22] PCT Filed: Jan. 31, 1996

[86] PCT No.: PCT/FR96/00161

§ 371 Date: Oct. 14, 1997

§ 102(e) Date: Oct. 14, 1997

[87] PCT Pub. No.: WO96/23800

PCT Pub. Date: Aug. 8, 1996

[30] Foreign Application Priority Data

Feb. 1, 1995 [FR] France ................ 95 01158

[51] Int. Cl.[6] .......... C22B 60/00; C01F 17/00; C07F 9/02; C07F 9/28
[52] U.S. Cl. .......... 423/9; 423/10; 423/21.5; 564/15; 210/634; 210/638; 210/643
[58] Field of Search .......... 564/15; 423/21.5, 423/9, 10; 976/DIG. 279; 210/638, 643, 634

[56] References Cited

U.S. PATENT DOCUMENTS

| 4,548,790 | 10/1985 | Horwitz et al. ............. 423/9 |
| 5,607,591 | 3/1997 | Dozol et al. ............. 210/638 |
| 5,717,126 | 2/1998 | Paciello et al. ............ 558/78 |

FOREIGN PATENT DOCUMENTS

| 2717480 | 9/1995 | France . |
| WO 94/24138 | 10/1994 | WIPO . |

OTHER PUBLICATIONS

Chem. Abstracts, vol. 114, No. 15, 15 Apr. 1991, Columbus, OH, US; Abstract No. 143712, Kondo Y et al.: Calixarene Derivatives having Phosphonic Acid Group XP002003481, & JP, A, 90 229 198 (Kanebo, Ltd.; Japan) 11 Sep. 1990.
Chemical Abstract 128:107566, 1996.
Chemical Abstract 125:86742, 1996.

Primary Examiner—Steven Bos
Attorney, Agent, or Firm—Pearne, Gordon, McCoy & Granger LLP

[57] ABSTRACT

The invention relates to novel calixarenes of formula:

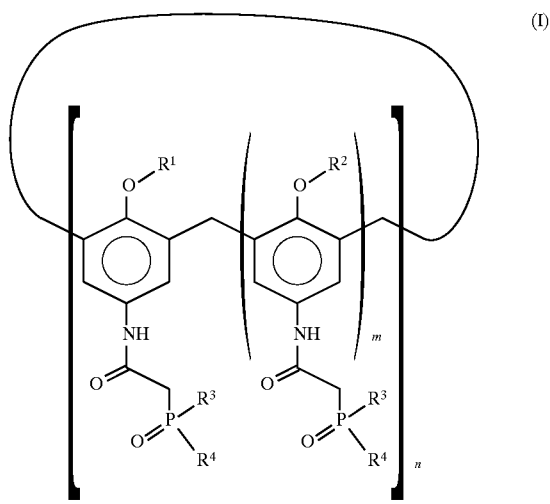

in which m is equal to 0 or 1, n is an integer from 2 to 8, with $4 \leq n(m+1) \leq 8$, $R^1$ and $R^2$, which can be the same or different, are alkyl or O-nitrophenoxyalkyl groups and $R^3$ and $R^4$, which can be the same or different, are alkyl or aryl groups.

The calixarenes can be used for extracting actinides and lanthanides from aqueous solutions from spent fuel reprocessing.

16 Claims, 1 Drawing Sheet

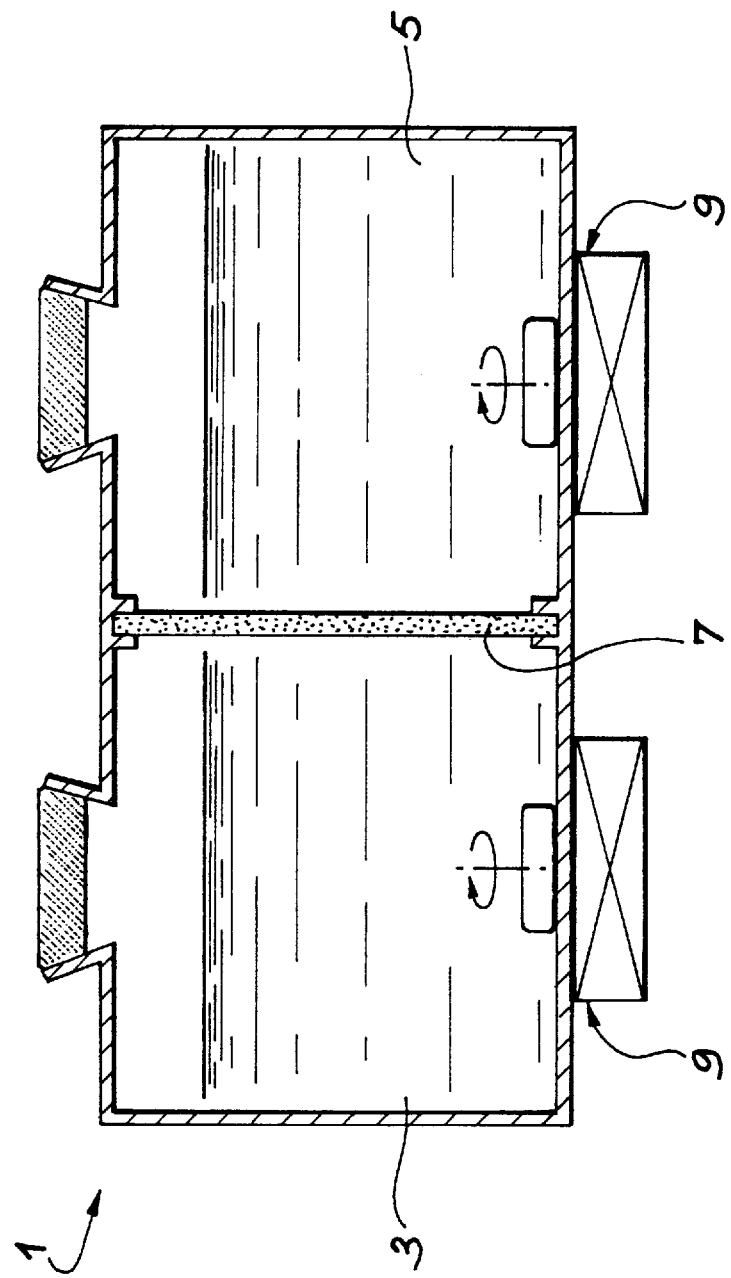

CALIXARENE DERIVATIVES, THEIR PREPARATION PROCESS AND THEIR USE FOR EXTRACTING ACTINIDES AND LANTHANIDES

The present invention relates to novel calixarenes derivatives, their preparation process and their use for extracting actinides and lanthanides.

More specifically, it relates to calixarenes having a phosphinoxidoacetamide substituent having interesting properties for extracting actinides and lanthanides, particularly trivalent lanthanides and actinides.

Therefore said novel calixarenes are usable for extracting actinides and lanthanides present in aqueous solutions, such as aqueous effluents from spent nuclear fuel reprocessing installations or spent nuclear fuel dissolving solutions.

Consideration has already been given to the use of macrocyclic ligands such as calixarenes for extracting metals from aqueous solutions. Thus, U.S. Pat. No. 4,477,377 describes the use of calixarenes for recovering cesium from aqueous solutions and WO 94/12502 and WO 94/24138 describe crown calixarenes usable for the selective extraction of cesium and actinides. In the first case, the calixarenes have a special structure, because they have several bridges giving an alternating 1, 3 constellation to the basic structure and giving them both the complexing properties of crown ethers and certain properties of calixarenes (lipophilic character, constellation, etc.).

The present invention relates to novel derivatives of calixarenes which, although having a greater mobility, have good extraction properties with respect to actinides and lanthanides, due to the presence of special substituents.

According to the invention, the calixarene is in accordance with the formula:

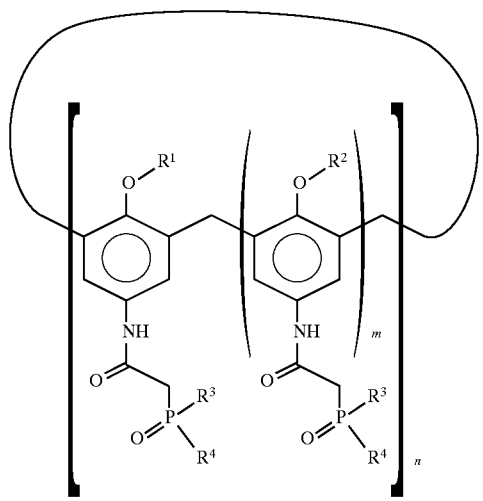

(I)

in which m is equal to 0 or 1,
n is an integer from 2 to 8, with $4 \leq n(m+1) \leq 8$,
$R^1$ and $R^2$, which can be the same or different, are alkyl or O-nitrophenoxyalkyl groups and
$R^3$ and $R^4$, which can be the same or different, are alkyl or aryl groups.

Thus, the calixarenes according to the invention have no bridge between the benzene units and consequently have a less rigid structure than that of the crown calixarenes of WO 94/12502 and WO 94/24138. In these novel calixarenes, the presence of phosphinoxidoacetamide groups, which are fixed to the upper edge of the cavity of the macrocycle, gives the ligand a very high affinity for actinides and lanthanides.

In the above formula (I), $R^1$ and $R^2$ can be alkyl or O-nitrophenoxyalkyl groups. The alkyl groups can be straight or branched and preferably have 1 to 18 carbon atoms.

In said formula, $R^3$ and $R^4$ can be alkyl or aryl groups. The alkyl groups can be straight or branched and preferably have 1 to 18 carbon atoms. The aryl groups which can be used are monovalent groups derived from an aromatic or heterocyclic nucleus by removing a hydrogen atom from one of the carbon atoms of the cycle. Examples of such groups are the phenyl, naphthyl, pyridyl, thiophenyl and substituted phenyl groups.

According to a first embodiment of the invention, the calixarenes are in accordance with formula (I) with m equal to 0. Such calixarenes have the same substituents on each edge of the cavity of the macrocycle. They have good extracting properties relative to trivalent actinides and lanthanides.

According to a second embodiment of the invention, the calixarene is in accordance with formula (I) with m equal to 1.

In this case all the substituents on the upper edge of the cavity of the macrocycle are identical and give a lipophilic character to the macrocycle. However, the substituents on the lower edge of the cavity alternate, a methyl group being interposed between two alkyl groups.

Such more soluble calixarenes, particularly in nitrophenyl alkyl ethers, are of interest for the extraction of tetravalent plutonium.

The calixarenes according to the invention can be prepared by a process having the following stages:

a) nitration of an O-alkyl calixarene of formula:

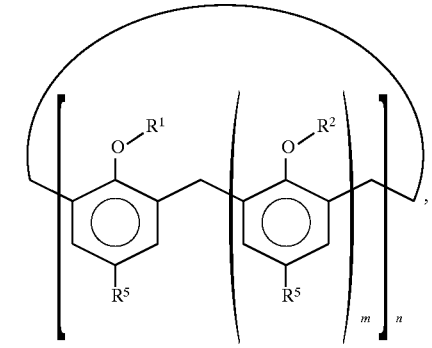

(II)

in which $R^1$, $R^2$, m and n have the meanings given hereinbefore and $R^5$ is a hydrogen atom or a tert. butyl group, in order to obtain a nitro derivative of formula:

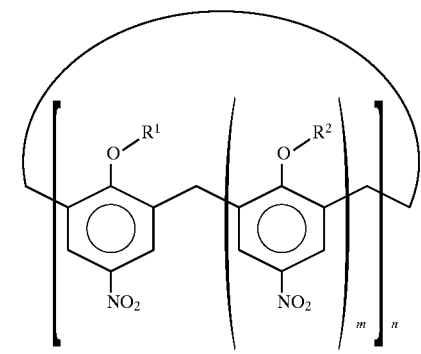

(III)

b) conversion of the nitro derivative of formula (III) into an amino derivative of formula:

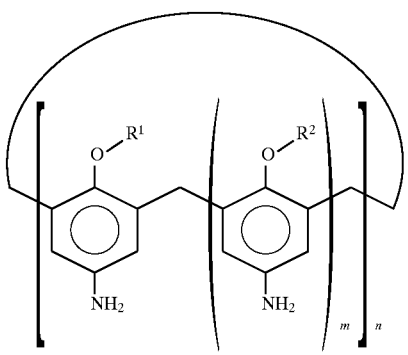
(IV)

by catalytic hydrogenation,
c) reacting the amino derivative of formula (IV) with a phosphinoxyidoacetate of formula:

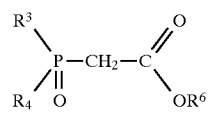
(V)

in which $R^3$ and $R^4$ have the meanings given hereinbefore and $R^6$ represents a group such as p-nitrophenyl or 2,4-dinitrophenyl.

In order to perform this process, the starting products are the corresponding O-alkyl calixarenes of formula (II), which firstly undergo a nitration to replace $R^5$ by $NO_2$, followed by a reduction of the nitro group into an amino group and a reaction of the amino group with an appropriate phosphinoxidoacetate of formula (V).

The phosphinoxidoacetate of formula (V) used in the final stage can be prepared from the corresponding methyl phosphinite of formula:

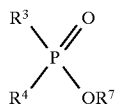
(VI)

where $R^3$ and $R^4$ have the meanings given hereinbefore and $R^7$ is an alkyl group with 1 to 4 carbon atoms, by reaction thereof with ethyl bromoacetate, followed by hydrolysis and esterification of the acid obtained with nitrophenol.

In the case where the calixarene corresponds to formula (I) with m equal to 1, the starting product can be obtained by preparing firstly a 1,3-di or 1,3,5-tri or 1,3,5,7-tetra-O-alkyl calixarene from the corresponding calixarene by reacting with potassium carbonate and alkyl bromide, followed by a methylation of the alkyl calixarene obtained by reacting it with methyl iodide.

The calixarenes according to the invention can be used for extracting at least one metal chosen from among the actinides and lanthanides present in an aqueous solution, particularly an acid solution, such as dissolving solutions and aqueous effluents from spent nuclear fuel reprocessing installations.

In order to carry out said extraction, contacting takes place between a first aqueous solution containing the metal or metals to be extracted and an immiscible liquid phase incorporating at least one calixarene according to formula (I), followed by reextraction in a second aqueous solution containing a complexing agent of the extracted metal or metals, initially transferred into the immiscible phase.

The immiscible phase can be a solid or liquid phase. In the case of a solid phase, it can be impregnated with one or more calixarenes according to the invention, in the pure state or in solution in an appropriate solvent. It is also possible to use a solid phase on which are grafted the calixarene or calixarenes according to the invention.

According to a first embodiment of the extraction, use is made of a liquid phase. This immiscible liquid phase is generally constituted by a solution of the calixarene or calixarenes according to the invention in an appropriate organic solvent.

With said liquid phase it is possible to reextract the cations (metals) by contacting said organic phase with a second liquid phase, in which selective recovery takes place of the metal or metals. The organic phase can then be reused.

According to a second embodiment of the extraction, the organic phase is immobilized in a solid support such as polypropylene. It is thus possible to transfer the actinides only from the first aqueous phase to a second aqueous phase (supported liquid membrane).

In this second embodiment, the immiscible phase is constituted by a liquid membrane incorporating the calixarene or calixarenes, one of the faces of the membrane being in contact with the first aqueous solution containing the metals to be extracted and the other face being in contact with the second, aqueous reextraction solution. The liquid membrane can e.g. be a supported liquid membrane constituted by a microporous membrane serving as a support and whose pores are filled with calixarene(s) in solution in an appropriate organic solvent.

This microporous membrane can be of polypropylene, polyvinylidene fluoride or polytetrafluoroethylene and can serve as a separation between a first compartment in which the first aqueous solution to be treated is located and a second compartment in which is located the second, aqueous reextraction solution.

In order to obtain a good extraction with supported liquid membranes, it is advantageous to use membranes having a limited thickness, a high porosity and a small pore diameter. These membranes can be used in the form of modules such as ultrafiltration or microfiltration modules having planar membranes or hollow fibres, which make it possible to treat large fluid flows.

According to the invention, the second, aqueous reextraction solution is an aqueous complexing agent solution. The complexing agent can be an organic acid or an organic acid salt such as methylene diphosphonic acid, oxalic acid, citric acid, oxalates and citrates. The use of such solutions makes it possible to carry out reextraction with high yields.

For performing the process according to the invention with a liquid phase, contacting of the aqueous solution with said immiscible liquid phase can take place in conventional liquid-liquid extraction installations, such as mixer-settlers, centrifugal extractors, pulsed columns, etc., but also by means of supported liquid membranes.

Generally the calixarene is dissolved in an appropriate support for forming the immiscible liquid phase. Examples of solvents which can be used are alkyl benzene and nitrophenyl alkyl ethers. Preferably the solvent is constituted by an ether such as orthonitrophenyl hexyl ether.

The calixarene concentration of the immiscible liquid phase is in particular dependent on the solvent used. It is possible to use concentrations from $10^{-4}$ to $5.10^{-2}$ mole/l, e.g. a concentration of $10^{-3}$ mole/l.

After extraction, it is possible to recover the actinides and lanthanides present in the immiscible liquid phase in a second aqueous solution containing a complexing agent of the extracted metals, such as those described hereinbefore.

Other features and advantages of the invention can be gathered from the following description of illustrative and non-limitative embodiments with reference to FIG. 1, which diagrammatically shows an extraction device using a supported liquid membrane.

EXAMPLE 1

Preparation of 25, 26, 27, 28 tetradodecyloxy-tetra-5, 11, 17, 23-(diphenyl phosphinoxidoacetamido) calix[4]arene (compound No. 1)

This compound is in accordance with formula (I) with m=0, n=4, $R^1=C_{12}H_{25}$, and $R^3=R^4$=phenyl.

1) Preparation of tetra-O-dodecyl-tetra-p-t-butyl-calix[4]arene

A suspension of 7.78 g (12 mmole) of tetra-p-t-butylcalix[4]arene and 15 g of NaH (60% in oil) is stirred in 400 ml of dimethyl formamide (DMF) for 1 to 1.5 hours under argon. This is followed by the addition of 35.89 g (34.5 ml, 144 mmole) of dodecyl bromide and stirring is continued for 5 days at ambient temperature. After destroying the excess NaH by adding 20 to 50 ml of water in careful manner, the liquid is decanted and the adhesive precipitate is washed in a bottle several times with small aliquot portions of petroleum ether. The crude product is distributed between 300 ml of chloroform and 300 ml of 15% hydrochloric acid. The organic layer is washed twice with brine, dried on anhydrous $Na_2SO_4$ and the solvent is eliminated in vacuo. The residue is dissolved in 100 ml of chloroform. After adding 700 ml of ethanol and storing in a refrigerator for several days, 7.9 to 11.9 g of a precipitate of a substantially pure product are obtained (yield 50 to 75%). This operation is repeated several times in order to obtain the desired degree of purity.

The characteristics of the product obtained are as follows:
$^1$H NMR (200 MHz, $CDCl_3$): 6.75 (s, ArH, 8 H) 4.45 (d, J=13.8 Hz, $ArCH_2Ar$, 4 H), 3.61 (t, J=6.8 Hz, $OCH_2$, 8 H) 3.25 (d, J=13.8 Hz, $ArCH_2Ar$, 4 H), 1.89 (m, $OCH_2CH_2$, 8 H), 1.42–1.19 (br m other $CH_2$ of the alkyl chain, 72 H), 1.05 (s, $C(CH_3)_3$, 36 H), 0.89 (t, J=6.4 Hz, $CH_3$, 12 H). $^{13}$C NMR (50 MHz, $CDCl_3$) 153.8; 144.1; 133.9; 124.9 ($C_{ar}$), 75.5 ($OCH_2$), 33.8–29.4 (a few signals covered partly due to $ArCH_2Ar$, $C(CH_3)_3$, $C(CH_3)_3$ and to the aliphatic chain); 26.4; 22.7; 14, 1 (last three C of the chain).

Elementary analysis: calculated for $C_{92}H_{152}O_4$ (1322.2): C 83.57%, H 11.59%; found C 83.19% H 11.34% FD-MS: m/z-1322.7. Melting point F=76°–78° C.

2) Preparation of tetra-O-dodecyl tetranitrocalix[4]arene 9.26 g (7 mmole) of tetra-O-dodecyl-tetra-t-butyl-calix[4]arene obtained previously are dissolved in 500 ml of dry methylene chloride at ambient temperature and are mixed with 80 ml of glacial acetic acid. This is followed by the dropwise addition of 24 ml of 100% nitric acid over 20 to 30 min, accompanied by vigorous stirring. After 1 to 4 hours, when the colour of the solution changes from dark violet to orange yellow, addition takes place of 250 ml of water and stirring is continued for an additional 30 min. The organic layer is separated, neutralized with a dilute sodium carbonate solution, washed with salt water, dried on anhydrous $Na_2SO_4$, evaporated in vacuo and the residue is dissolved in 30 to 70 ml of chloroform. Careful addition takes place of 500 to 600 ml of methanol and a crude product precipitate is obtained in the form of a largely colourless solid. It is purified by recrystallization from n-heptane. This gives 7.60 g of product (yield 85%).

The characteristics of the product obtained are as follows:
$^1$H NMR (200 MHz, $CDCl_3$): 7.55 (s, ArH, 8 H) 4.48 (d, J=13.8 Hz, $ArCH_2Ar$, 4 H), 3.95 (t, J=6.8 Hz, $OCH_2$, 8 H), 3.37 (d, J=13.8 Hz, $ArCH_2Ar$, 4 H), 1.89 (m, $OCH_2CH_2$, 8 H), 1.42–1.19 (br m, other $CH_2$ of the alkyl chain, 72 H), 0.89 (t, J=6.4 Hz, $CH_3$, 12 H). $^{13}$C NMR (50 MHz, $CDCl_3$): 161.6; 142.8; 135.4; 123.9 ($C_{ar}$), 76.4 ($OCH_2$), 31.9–29.4 (a few signals covered partly due to $ArCH_2Ar$ and to the aliphatic chain), 26.1, 22.6, 14.05 (last three C of the chain).

Elementary analysis: calculated for $C_{76}H_{116}O_{12}N_4$ (1277.8): C 71.44%, H 9.15%, N 4.38%; found C 71.29%, H 8.97%, N 4.19%. FD-MS: m/z=1277.0; F: 117°–188° C.

3) Preparation of tetra-O-dodecyl tetraaminocalix[4]arene 6.39 g (5 mmole) of tetra-O-dodecyl tetranitrocalix[4]arene obtained in 2) are dissolved in 300 ml of hot toluene and hydrogenation takes place under atmospheric pressure in the presence of Raney nickel at 60° C. When the reaction is ended, the catalyst is eliminated by filtration, washing takes place with hot toluene and the toluene solution is evaporated in vacuo. The residue is recrystallized from isopropanol. This gives 4.63 g of compound (yield 80%).

The characteristics of the product obtained are as follows:
$^1$H-NMR (200 MHz, $CDCl_3$): 6.05 (s, ArH, 8 H), 4.29 (d, J=13.1 Hz) $ArCH_2Ar$, 4 H), 3.74 (t, J=7.2 Hz, $OCH_2$, 8H), 2.90 (d, J=13.1 Hz, $ArCH_2Ar$, 4 H), 2.75 (br, s, $NH_2$, 8 H), 1.84 (m, $OCH_2CH_2$, 8 H), 1.26 (br, m, $CH_2$ of alkyl chains, the number of H being dependent on the length), 0.87 (t, J=6.5 Hz, $CH_3$, 12 H). $^{13}$C-NMR (50 MHz, $CDCl_3$): 150.0; 140.3; 135.6; 115.7 ($C_{ar}$), 75.1 ($OCH_2$), 32.0–29.3 (a few signals covered partly due to $ArCH_2Ar$ and to the aliphatic chain); 26.4; 22.7; 14.1 (last three C of the chain).

Elementary analysis: calculated for $C_{76}H_{124}O_4N_4$ (1157.9): C 78.84%, H 10.79%, N 4.84%; found C 78.81%, H 10.79%, N 4.84% FD-MS: m/z=1157.7; F: 163° C.

4) Preparation of nitrophenyl diphenyl phosphinoxidoacetate a) Preparation of diphenyl phosphinoxidoacetic acid.

43 g (0.2 mole) of methyl diphenyl phosphinite and 25 ml of ethyl bromoacetate are mixed in a 500 ml open bottle at ambient temperature. After a few seconds, the mixture is rapidly heated and the methyl bromide is eliminated. When the violent reaction has ended, the solution is heated to 100° C. for 30 min. The crude product is added to a solution of 40 g of NaOH in 300 ml of a water-ethanol mixture (1:1 by volume) and it is kept under argon at 70° C. for three days. The ethanol is then evaporated, 200 ml of water are added and said solution is extracted with 100 ml of chloroform to eliminate the undesired Arbuzov rearrangement products. The aqueous layer is acidified at a pH of 1 and the crude diphenyl phosphinoxidoacetic acid is extracted with chloroform (3×200 ml). The combined chloroform extracts are washed with salt water, dried on $Na_2SO_4$ and evaporated in vacuo. If the acid appears as an oil crystallization is accelerated by treating the oil with benzene. This gives the acid with a yield of 80 to 90%.

b) Preparation of nitrophenyl diphenyl phosphinoxidoacetate.

2.60 g (10 mmole) of the diphenylphosphinoxidoacetic acid obtained in a) and 1.67 g of p-nitrophenol (20% excess) are dissolved in 50 ml of hot chloroform, followed by the addition of 2.06 g of dicyclohexyl carbodiimide (DCC). The mixture is stirred for one night at ambient temperature. Elimination takes place by filtration of the dicyclohexyl urea formed (DCU). Most of the residual DCU is precipitated by adding 75 to 100 ml of ethyl acetate and storage in the refrigerator for 30 to 60 min. After a second filtration, the filtrate is evaporated to dryness and the residue recrystallized from ethyl acetate. The addition of heptane to the mother liquor makes it possible to again obtain the product. The total yield is approximately 80% of products sufficiently pure for the following synthesis.

The product has the following characteristics:

$^1$H NMR (200 MHz, CDCl$_3$): 8.16 (d, J=9.2 Hz, NO$_2$ArH), 2 H), 7.89–7.31 (m other ArH, 10 H), 6.94 (d, J=9.2 Hz, NO$_2$ArH, 2 H), 3.75 (d, J=14.5 Hz, CH$_2$PO, 2 H).

5) Preparation of tetra-O-dodecyl tetrakis (diphenyl phosphinoxidoacetamido)calix[4]arene. (Compound No. 1)

Stirring takes place in 50 ml of dry chloroform and free from ethanol of 289 mg (0.25 mmole) of tetra-O-dodecyl tetra-p-amino calix[4]arene obtained in 3) and 700 mg of nitrophenyl diphenyl phosphinoxidoacetate obtained in 4), at 45° C. for 3 days. After cooling to ambient temperature, 50 ml of water and a few ml of a concentrated potassium hydroxide solution are added. The mixture is stirred for 3 to 4 hours, followed by the separation of the organic layer and successive washing with a 5% sodium carbonate solution, water and salt water. After drying on anhydrous Na$_2$SO$_4$, the solvent is eliminated in vacuo and the residue recrystallized in methanol. This gives 372 mg of compound 1 (yield 70%).

The compound has the following characteristics:

$^1$H NMR (200 MHz, CDCl$_3$): 8.96 (s, NH, 4 H), 7.75–7.37 (m, P-ArH, 40 H), 6.56 (s, calix-ArH, 8 H), 4.29 (d, J=13.2 Hz, ArCH$_2$, Ar, 4 H), 3.74 (t, J=7.2 Hz, OCH$_2$, 8 H), 3.42 (d, J=13.6 Hz, POCH$_2$CO, 8 H), 2.99 (d, J=13.2 Hz, ArCH$_2$, Ar, 4 H); 1.81 (m, OCH$_2$CH$_2$, 8 H), 1.26 (br, m, CH$_2$ of alkyl chains, 72 H), 0.87 (t, J=6.5 Hz, CH$_3$, 12 H). The associated water coming from the solvent appears as a wide singlet in the region of approximately 2 ppm.

$^{13}$C NMR (50 MHz, CDCl$_3$): 163.1 (d, J=4.6 Hz, CONH), 154.0, 35.0–128.7, 122.1 (partly covered C$_{Ar}$), 75.3 (OCH2), 3.97 (d, J=59.2 Hz, CH$_2$PO), 32.0–29.5) (a few signals partly covered due to ArCH$_2$Ar and to the aliphatic chain), 26.1, 22.6, 14.0 (three last C of the chain). FAB-MS: 2129.2.

The melting point is not distinct, the sample melting after softening in a temperature range of approximately 150° to 180° C. with decomposition.

EXAMPLES 2 to 5

In these examples the same operating procedure as in example 1 is followed for preparing compounds 2 to 5 of table 1. The characteristics of the intermediate tetraamino compounds are as follows:

Intermediate of compound 2

FD-MS: m/z=1045.0; F=178° C. elementary analysis calculated for C$_{68}$H$_{108}$O$_4$N$_4$C 78.11%, H 10.41%, N 5.36%; found 78.24%, H 10.29%, N 5.36%.

Intermediate of compound 3

FD-MS: m/z=1269.1; F: 148° C. elementary analysis calculated for C$_{84}$H$_{140}$O$_4$N$_4$: C 79.44%, H 11.11%, N 4.41%; found: C 79.38%, H 11.12%, N 4.40%.

Intermediate compound 4

FD-MS: m/z=1382.6 F: 140° C. elementary analysis calculated for C$_{92}$H$_{156}$O$_4$N$_4$: C 79.94%, H 11.38%, N 4.05%; found C 78.53%, H 11.26%, N 4.05%.

Intermediate compound 5

FD-MS: m/z=1495.9 F: 135° C. elementary analysis calculated for C$_{100}$H$_{172}$O$_4$N$_4$: C 80.37%, H 11.60%, N 3.75%; found C 78.29%, H 11.37%, N 3.70%.

The characteristics of compounds 2 to 5 are as follows:

Characteristics of Compound 2: tetra-O-decyl
tetrakis (diphenyl phosphinoxidoacetamido)calix[4]
arene $^1$H NMR (200 MHz, CDCl$_3$): 8.96 (s, NH, 4 H), 7.75–7.37 (m, P-ArH, 40 H), 6.56 (s, calix-ArH, 8H, 4.29 (d, J=6 13.2 Hz, ArCH$_2$Ar, 4H), 3.74 (t, J=7.2 Jz, OCH$_2$, 8 H), 3.42 (d, J=13.6 Hz, POCH$_2$CO, 8H), 2.99 (d, J=13.2 Hz) ArCH$_2$Ar, 4 H), 1.81 (m, OCH$_2$CH$_2$, 8 H), 1.26 (br, m, CH$_2$ of alkyl chains, 56 H); 0.87 (t, J=6.5 Hz, CH$_2$, 12 H). The associated water (clearly coming from the solvent) appears as a wide singlet in the region at approximately 2 ppm.

$^{13}$C NMR (50 MHz, CDCl$_3$): 163.1 (d, J=4.6 Hz, CONH), 154.0, 135.0–128.7, 122.1 (partly covered CAr), 75.03 (OCH$_2$), 39.7 (d, J=59.2 Hz, CH$_2$PO), 32.0–29.5 (a few signals partly covered due to ArCH$_2$Ar and to the aliphatic chain), 76.1, 22.6, 14.0 (three last C of the chain). FAB-MS: 2016.8 (calculated 2014.5).

The melting point is not distinct, the sample melting after softening in a temperature range of approximately 150° to 180° C. with decomposition.

Characteristics of Compound 3: tetra-O-tetradecyl
tetrakis (diphenyl-phosphinoxidoacetamido)calix[4]
arene $^1$H NMR (200 MHz, CDCl$_3$): 8.96 (s, NH, 4 H), 7.75–7.37 (m, P-ArH, 40 H), 6.56 (s, calix-ArH, 8H), 4.29 (d, J=13.2 Hz, ArCH$_2$Ar, 4H), 3.74 (t, J=7.2 Hz, OCH$_2$, 8 H), 3.42 (d, J=13.6 Hz, POCH$_2$CO, 8H) 2.99 (d, J=13.2 Hz, ArCH$_2$Ar, 4H), 1.81 (m, OCH$_2$CH$_2$, 8H), 1.26 (br, m, CH$_2$ of alkyl chains, 88 H); 0.87 (t, J=6.5 Hz, CH$_3$, 12H). The associated water (clearly coming from the solvent) appears as a wide singlet in the region at approximately 2 ppm.

$^{13}$C NMR (50 MHz, CDCl$_3$): 163.1 (d, J=4.6 Hz, CONH), 154.0, 135.0–128.7, 122.1 (partly covered C$_{Ar}$), 75.3 (OCH$_2$), 39.7 (d, J=59.2 Hz, CH$_2$PO), 32.0–29.5 (a few signals partly covered due to ArCH$_2$Ar and to the aliphatic chain), 26.1, 22.6, 14.0 (three last C of the chain). FAB-MS: 2241.5 (calculated 2238.9).

The melting point is not distinct, the sample melting after softening in a temperature range of approximately 150° to 180° C. with decomposition.

Characteristics of Compound 4: tetra-O-hexadecyl
tetrakis(diphenyl-phosphinaxidoacetamido)calix[4]
arene $^1$H NMR (200 MHz, CDCl$_3$, 8.96 (s, NH, 4H), 7.75–7.37 (m,PArH, 40H), 6.56 (s, calix-ArH, 8H), 4.29 (d, J=13.2 Hz, ArCH$_2$Ar, 4H), 3.74, (t, J=7.2 Hz, OCH$_2$, 8H), 3.42 (d, J=13.6 Hz, POCH$_2$CO, 8H), 2.99 (d, J=13.2 Hz, ArCH$_2$Ar, 4H), 1.81 (m, OCH$_2$CH$_2$, 8H), 1.26 (br m, CH$_2$ of alkyl chains, 104 H); 0.87 (t, J=6.5 Hz, CH$_3$, 12 H). The associated water (clearly coming from the solvent) appears as a wide singlet in the region of approximately 2 ppm.

$^{13}$ C NMR (50 MHz, CDCl$_3$); 163.1 (d, J=4.6 Hz, CONH), 154.0, 135.0–128.7, 122.1 (partly covered C$_{Ar}$), 75.3 (OCH$_2$), 39.7 (d, J=59.2 Hz, CH$_2$PO), 32.0–29.5 (a few signals partly covered due to ArCH$_2$Ar and to the aliphatic chain), 26.1, 22.6, 14.0 (three last C of the chain). FAB-MS; 2353.9 (calculated 2351.1). The melting point is not distinct, the sample melting after softening in a temperature range of approximately 150 to 180° C. with decomposition.

Characteristics of compound 5: tetra-O-octadecyl
tetrakis(diphenyl-phosphinoxidoacetamido(calix[4]
arene $^1$H NMR (200 MHz, CDCl$_3$): 8.96 (s, NH, 4H), 7.75–7.37 (m, P-ArH, 40 H), 6.56 (s, calix-ArH, 8H), 4.29 (d, J=13.2 Hz, ArCH$_2$Ar, 4H), 3.74 (t, J=7.2 Hz, OCH$_2$, 8H), 3.42 (d, J=13.6 Hz, POCH$_2$CO, 8H), 2.99 (d, J=13.2 Hz, ArCH$_2$Ar, 4H), 181 (m, OCH$_2$CH$_2$, 8H), 1.26 (br m, CH$_2$ of alkyl chains 120 H); 0.87 (t, J=6.5 Hz, CH$_3$, 12 H). The associated water (clearly coming from the solvent, appears as a wide singlet in the region of approximately 2 ppm.

$^{13}$C NMR (50 MHz, CDCl$_3$); 163.1 (d, J=4.6 Hz, CONH), 154.0, 135.0–128.7, 122.1 (partly covered C$_{Ar}$), 75.3 (OCH$_2$), 39.7 (d, J=59.2 Hz, CH$_2$PO), 32.0–29.5 (a few signals partly covered due to ArCH$_2$Ar and to the aliphatic chain), 26.1, 22.6, 14.0 (three last C of the chain). FAB-MS: 2466.2 (calculated 2463.4).

The melting point is not distinct, the sample melting after softening in a temperature range of approximately 150° to 180° C. with decomposition.

EXAMPLE 6

Preparation of 25, 27 didecyloxy-26,28-dimethoxy-5,11, 17,23-(diphenylphosphinoxido-acetamido) calix[4]arene (compound No. 6)

The compound is in accordance with formula (I) with m=1, n=2, R$^1$=decyl, R$^2$=methyl and R$^3$/R$^4$=phenyl.

1) Preparation of 25,27 didecyloxy calix[4]arene

Refluxing takes place for 24 hours of a mixture of 13.5 mmole (10 g of calix[4]arene), 15 mmole (2.1 g) of K$_2$CO$_3$ and 27.5 mmole of decyl bromide in 150 ml of acetonitrile. After evaporating the solvent, the residue is dissolved in chloroform, washed with 1N HCl (2×30 ml) and then with salt water. The organic layer is dried on anhydrous Na$_2$SO$_4$ and the solvent is eliminated in vacuo. The residue is recrystallized from chloroform/methanol. The alkyl derivative is obtained with a 70 to 85% yield.

2) Preparation of 25.27 didecyloxy-26,28-dimethoxy calix[4]arene

Refluxing takes place of 6 mmole of the product obtained in 1) and 0.6 mole of NaH in a mixture of tetrahydrofuran/dimethyl formamide (DMF) with a ratio of 5:1 for 30 min. Dropwise addition takes place at ambient temperature of 0.6 mole of methyl iodide. The mixture is stirred for one night at 80° C. and then carefully treated with water to destroy the NaH which has not reacted. The solvents are eliminated in vacuo, the residue taken up in chloroform and washed with water. The organic layer is separated, dried on MgSO$_4$ and filtered. After evaporating the solvent, the crude product is taken up in a few ml of chloroform and filtered on silica with chloroform. The product is obtained in the form of a clear viscous oil with a 70 to 96% yield. It is sufficiently pure for performing the following stages.

3) Preparation of 25,27-didecyloxy-26,28-dimethoxy-5,11, 17,23 nitro calix[4]arene In order to prepare this compound, the operating procedure of example 1.2) is followed, starting with the product obtained in the preceding stage.

4) Preparation of 25,27-didecyloxy 26,28-dimethoxy-5,11, 17,23-tetra amino calix[4]arene For this preparation, the same operating procedure as in example 1.3 is followed, starting from the previously obtained product.

5) Preparation of compound 6

For this preparation the operating procedure of example 1.5) is followed. The characteristics of the compound obtained are: di-O-decyl di-O-methyltetrakis (diphenylphosphinoxidoacetamido) calix[4]arene.

Due to the greater constellation flexibility, the NMR spectrum is more complicated than the spectrum of compounds with 4 identical O-alkyl residues.

$^1$H NMR (200 MHz, CDCl$_3$): 9.48, 9.32, 9.08 (3s, NH together 4H), 7.95–7.27 (m, P-ArH, 40 H), 6.78, 6.07, 5.93 (3s, calix-ArH, together 8H), 4.24–2.77 (ArCH$_2$Ar, OCH$_2$, OCH$_3$, POCH$_2$CO, 26 II), 1.97–0.83 (br m, alkyl chains, 38 H). FAB-MS: 1763.2 (calculated 1761.9).

The melting point is not distinct, the sample melting with softening in a temperature range of approximately 150° to 180° C. with decomposition.

Table 1 illustrates compounds 1 to 6 prepared in examples 1 to 6, as well as compounds 7 to 10 prepared in an identical manner.

EXAMPLES 7 to 16

In these examples, an evaluation takes place of the effectiveness of the calixarenes of table 1 for extracting plutonium, neptunium and americium, as well as europium (simulating all the trivalent lanthanides) of an aqueous solution containing one of these elements. The composition of the aqueous solution is as follows:

HN0$_3$: 1 mmole/l

NaN0$_3$: 4 mole/l pH: ≈0

Pu 0.6 mg/l

Am 0.02 mg/l

Np: 200 mg/l

Eu: ≦0.001 mg/l

In these examples, contacting takes place of 3 ml of aqueous solution with 3 ml of an organic solution constituted by nitrophenyloctylether containing 0.001 or 0.0001 mole/l of the calixarene used. Contacting takes place in a 20 ml polypropylene tube, which undergoes stirring. After 1 hour of contacting, the two phases are allowed to settle and the activity of each phase is counted by liquid scintillation or α and γ spectrometries.

The distribution coefficient D is then determined and this corresponds to the ratio of the activity of actinide in the organic phase to the activity of actinide in the aqueous phase.

The results obtained are given in table 2.

This table also shows for comparative purposes the results obtained on using for extraction CMPO with a concentration of 0.01 mole/l in nitrophenyl hexyl ether.

EXAMPLES 17 to 26

These examples use the second embodiment of the process according to the invention for extracting europium, neptunium, plutonium and americium from aqueous solutions having the same compositions as those used in examples 7 to 16. These examples use the device shown in the attached drawing.

This device comprises an enclosure 1 subdivided into two compartents 3 and 5 by a supported liquid membrane 7, constituted by a microporous polypropylene membrane marketed under the name CELGARD 2500 and having the following characteristics:

porosity factor: 0.45 pore diameter: 0.04 μm membrane thickness: 0.025 mm.

The pores of this membrane are filled with an organic phase constituted by nitrophenylhexyl ether incorporating 0.001 or 0.0001M of calixarene.

The two compartments 3 and 5 are equipped with magnetic stirrers 9.

Compartment 3 contains 50 ml of aqueous solution (NaNO$_3$:4 mole/l, HNO$_3$: 1mole/l with Eu, Np, Pu, Am); and compartment 5 contains 50ml of an aqueous reextraction solution constituted by an aqueous solution with 1 mole/l of methylene diphosphonic acid.

The two solutions are stirred and the initial activity of the solution of compartment 3 is determined, followed by the activity of the aqueous reextraction solution of compartment 5 by liquid α spectrometry and the operation is continued for one day. From it is deduced the percentage of neptunium, plutonium, americium and europium recovered in the aqueous reextraction solution after 6 and 24 h.

The calixarenes used, the permeability (in cm h$^{-1}$) of the membrane to Np and Pu, as well as the %, at the end of 6 and 24 h, of Eu, Am, Np and Pu recovered are given in table 3.

Table 3 makes it clear that the supported liquid membrane even when containing a small concentration of calixarenes ($10^{-3}$–$10^{-4}$M) is very effective for transporting Am and Pu into the aqueous reextraction solution (much more effective than $10^{-2}$M CMPO).

TABLE 1-continued

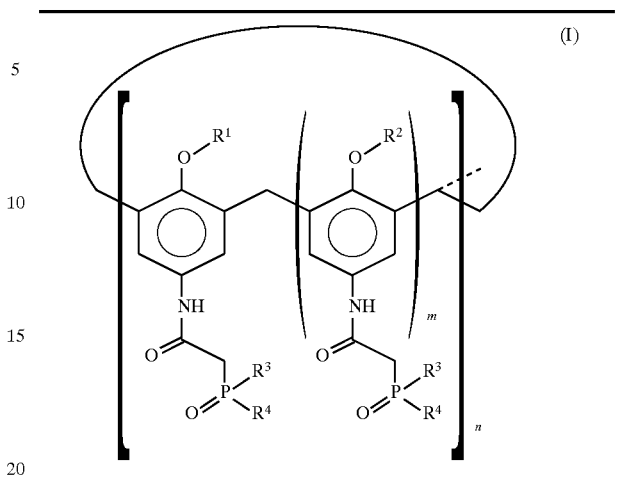

(I)

TABLE 1

| COMPOUND | m | n | R$^1$ | R$^2$ | R$^3$ | R$^4$ |
|---|---|---|---|---|---|---|
| 1 | 0 | 4 | C$_{12}$H$_{25}$ | — | C$_6$H$_5$ | C$_6$H$_5$ |
| 2 | 0 | 4 | C$_{10}$H$_{21}$ | — | C$_6$H$_5$ | C$_6$H$_5$ |
| 3 | 0 | 4 | C$_{14}$H$_{29}$ | — | C$_6$H$_5$ | C$_6$H$_5$ |
| 4 | 0 | 4 | C$_{16}$H$_{33}$ | — | C$_6$H$_5$ | C$_6$H$_5$ |
| 5 | 0 | 4 | C$_{18}$H$_{37}$ | — | C$_6$H$_5$ | C$_6$H$_5$ |
| 6 | 1 | 2 | C$_{10}$H$_{21}$ | CH$_3$ | C$_6$H$_5$ | C$_6$H$_5$ |
| 7 | 1 | 2 | C$_{18}$H$_{37}$ | CH$_3$ | C$_6$H$_5$ | C$_6$H$_5$ |
| 8 | 0 | 4 | C$_5$H$_{11}$ | — | C$_6$H$_5$ | C$_6$H$_5$ |
| 9 | 1 | 2 | C$_8$H$_{17}$ | CH$_3$ | C$_6$H$_5$ | C$_6$H$_5$ |
| 10 | 0 | 4 | 2Ethyl Hexyl | — | C$_6$H$_5$ | C$_6$H$_5$ |

TABLE 2

| | | D(distribution coefficient) | | | |
|---|---|---|---|---|---|
| Ex | COMPOUND | 152-Eu | 237-Np | 239-Np | 241-Np |
| 7 | n°2 0.001M | >100 | 2 | 90 | 100 |
| 8 | n°1 0.001M | — | 4 | >100 | >100 |
| 9 | n°3 0.001M | >100 | 1.8 | 90 | >100 |
| 10 | n°4 0.0001M | — | 1.1 | 27 | 27 |
| 11 | n°5 0.0001M | — | 1.5* | 24* | 21* |
| 12 | n°6 0.001M | >100 | 3 | 130 | 240 |
| 13 | n°7 0.001M | >100 | 3 | 170 | 250 |
| 14 | n°8 0.001M | >100 | 2* | 100* | 250* |
| 15 | n°9 0.001M | >100 | 2 | 110 | 280 |
| 16 | n°10 0.0005M | 1.5 | 2 | 20 | 4.5 |
| COMPARATIVE | CMPO 0.01M | — | 0.85 | 22 | 1.2 |

NB: * = precipitation

CMPO = 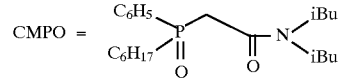

TABLE 3

| | | Permeability (cm/h) | | | | Percentage transported in 6 h. | | | | Percentage transported in 24 h. | | | |
|---|---|---|---|---|---|---|---|---|---|---|---|---|---|
| Ex | Compound | 152 Eu | 237 Np | 239 Pu | 241 Am | 152 Eu | 237 Np | 239 Pu | 241 Am | 152 Eu | 237 Np | 239 Pu | 241 Am |
| 17 | N °2 | — | 3 | 3.6 | 5 | — | 73 | 82 | 95.5 | — | 80 | 83 | 100 |
| 18 | N °1 | 2.75 | 1.35 | 3.4 | 4.9 | 95 | 56 | 84 | 97 | 100 | 66 | 85 | 100 |
| 19 | N °3 | 2.8 | 1.3 | 2.95 | 5.3 | 90 | 54 | 84 | 98 | 98 | 62 | 88 | 100 |
| 20 | N °4 | — | 0.46 | 1.4 | 0.08 | — | 21 | 54 | 3 | — | — | — | — |
| 21 | N °5 | — | — | — | — | — | — | — | — | — | — | — | — |
| 22 | N °6 | — | 1.6 | 6.4 | 2.9 | — | 49.4 | 97.1 | 94.2 | — | 68.3 | 100 | 94.9 |
| 23 | N °7 | — | 1.3 | 7 | 3.2 | — | 42.7 | 99.7 | 92.6 | — | 59.4 | 100 | 99.3 |
| 24 | N °8 | — | <0.2 | 3.6 | 3.4 | — | 8.5 | 79.6 | 99 | — | 14.5 | 80 | 100 |
| 25 | N °9 | — | 1.6 | 4.2 | 2.9 | — | 52.4 | 84.1 | 91.3 | — | 75.2 | 86 | 100 |

TABLE 3-continued

| | | Permeability (cm/h) | | | | Percentage transported in 6 h. | | | | Percentage transported in 24 h. | | | |
|---|---|---|---|---|---|---|---|---|---|---|---|---|---|
| Ex | Compound | 152 Eu | 237 Np | 239 Pu | 241 Am | 152 Eu | 237 Np | 239 Pu | 241 Am | 152 Eu | 237 Np | 239 Pu | 241 Am |
| 26 | N °10 | — | 0.6 | 2 | 0.5 | — | 19.8 | 53.5 | 27.8 | — | 30.4 | 76.6 | 62.4 |
|  | CMPO | — | 0.74 | 3.44 | 0.17 | — | 50 | 99 | 9.8 | — | 68 | 100 | 45 |

We claim:

1. Calixarene of formula:

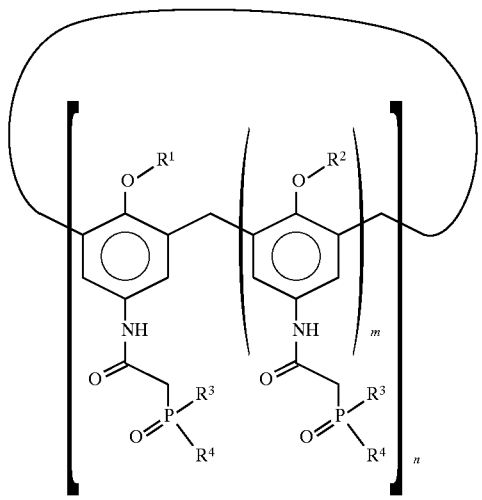

in which m is equal to 0 or 1, n is an integer from 2 to 8 with $4 \leq n(m+1) \leq 8$, $R^1$ and $R^2$, which can be the same or different, are alkyl or o-nitrophenoxyalkyl groups and $R^3$ and $R^4$, which can be the same or different, are alkyl or aryl groups.

2. Calixarene according to claim 1, wherein m is equal to 0.

3. Calixarene according to claim 2, wherein n is equal to 4 and in that $R^3$ and $R^4$ are each a phenyl group.

4. Calixarene according to claim 3, wherein $R^1$ is an alkyl group chosen from among decyl, dodecyl, tetradecyl, hexadecyl, octadecyl, pentyl and 2-ethylhexyl groups.

5. Calixarene according to claim 1, wherein m is equal to 1.

6. Calixarene according to claim 5, wherein n is equal to 2, $R^1$ is an octyl, decyl or octadecyl group, $R^2$ is a methyl group and $R^3$ and $R^4$ are each a phenyl group.

7. Process for the preparation of calixarene according to formula (I) of claim 1, comprising the steps of:

a) nitrating an O-alkyl calixarene of formula:

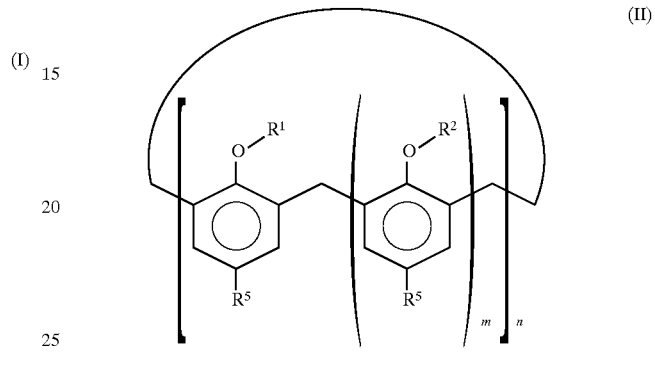

in which $R^1$, $R^2$, m and n have the meanings given in claim 1 and $R^5$ is a hydrogen atom or a tert butyl group, to obtain a nitro derivative of formula:

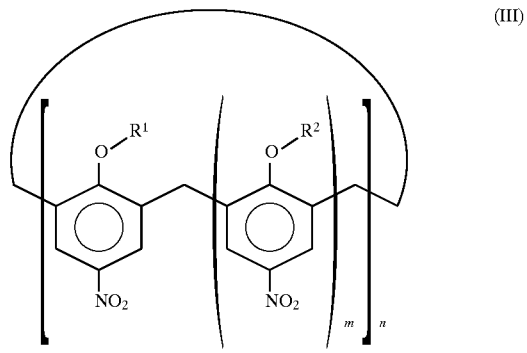

b) converting the nitro derivative of formula (III) into an amino derivative of formula:

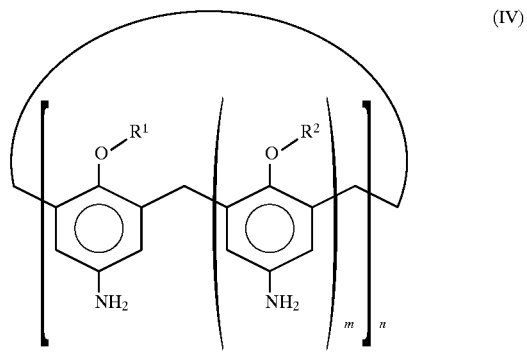

by catalytic hydrogenation, and c) reacting the amino derivative of formula (IV) with phosphinoxidoacetate of formula:

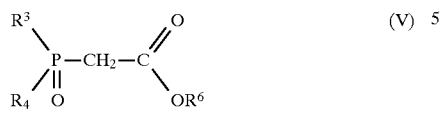 (V)

in which $R^3$ and $R^4$ have the same meanings as are recited in claim 1 and $R^6$ is a p-nitrophenyl or 2,4-dinitrophenyl group.

8. Process for the separation of at least one metal chosen from among the lanthanides and actinides present in a first aqueous solution, comprising the steps of: (a) contacting said first aqueous solution containing said at least one metal, with a phase immiscible with said first aqueous solution, said immiscible phase comprising a calixarene of formula:

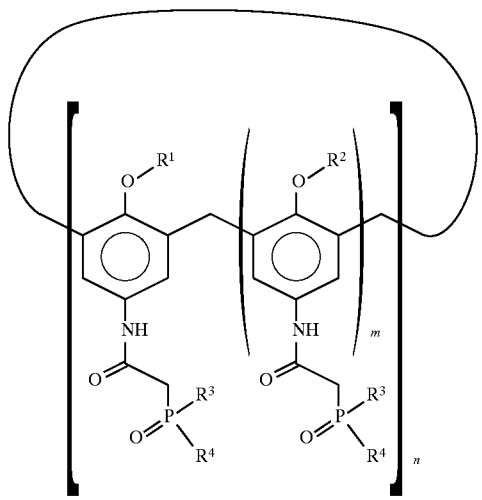 (I)

in which m is equal to 0 or 1, n is an integer from 2 to 8 with $4 \leq n(m+1) \leq 8$, $R^1$ and $R^2$, which can be the same or different, are alkyl or o-nitrophenoxyalkyl groups, and $R^3$ and $R^4$, which can be the same or different, are alkyl or aryl groups, whereby said at least one metal is extracted in said aqueous-phase, and (b) contacting said immiscible phase with a second aqueous solution comprising a complexing agent for said at least one metal whereby said at least one metal is reextracted in said second aqueous solution.

9. Process according to claim 8, wherein the immiscible phase is a solution of said calixarene in an organic solvent.

10. Process according to claim 9, wherein the organic solvent is a nitrophenylalkyl ether.

11. Process according to claim 9, wherein the immiscible phase is immobilized in a microporous membrane.

12. Process according to claim 11, wherein the microporous membrane is formed of polypropylene.

13. Process according to claim 11, wherein one of the faces of the membrane is in contact with the first aqueous solution and the other face of the membrane is in contact with the second solution.

14. Process according to claim 8, wherein the complexing agent is methylene diphosphonic acid.

15. Process according to claim 8, in which, in the formula of the calixarene, m is equal to 0, n is equal to 4 and $R^3$ and $R^4$ are each a phenyl group.

16. Process according to claim 8, in which, in the formula of the calixarene, m is equal to 1, $R^1$ is an octyl, decyl or octadecyl group, $R^2$ is a methyl group and $R^3$ and $R^4$ are each a phenyl group.

* * * * *